(12) United States Patent
Meyer

(10) Patent No.: US 6,790,201 B2
(45) Date of Patent: Sep. 14, 2004

(54) STRAP ASSEMBLIES AND METHODS OF USE THEREOF

(75) Inventor: Helen B. Meyer, 29744-290 St., Worthington, MN (US) 56187

(73) Assignee: Helen B. Meyer, Worthington, MN (US)

( * ) Notice: Subject to any disclaimer, the term of this patent is extended or adjusted under 35 U.S.C. 154(b) by 92 days.

(21) Appl. No.: 09/828,619

(22) Filed: Apr. 6, 2001

(65) Prior Publication Data

US 2002/0029406 A1 Mar. 14, 2002

Related U.S. Application Data

(60) Provisional application No. 60/195,033, filed on Apr. 6, 2000.

(51) Int. Cl.$^7$ ................................................. A61M 5/32
(52) U.S. Cl. ........................ 604/345; 224/257; 224/259; 224/260; 224/261; 224/262; 224/270; 224/625; 224/638; 604/179
(58) Field of Search ......................... 224/257, 259–262, 224/270, 625, 638, 626, 637; 604/174, 179, 345; 128/DIG. 6; D3/327; 142/3

(56) References Cited

U.S. PATENT DOCUMENTS

| | | | | |
|---|---|---|---|---|
| 1,816,262 A | * | 7/1931 | Ritter | 297/484 |
| 3,184,883 A | * | 5/1965 | McCook | 446/28 |
| 4,087,864 A | | 5/1978 | LaBove et al. | |
| 4,168,022 A | * | 9/1979 | Brewer | 224/257 |
| 4,320,863 A | * | 3/1982 | Lyer et al. | 224/259 |
| 4,504,267 A | | 3/1985 | Parmelee et al. | |
| 4,582,508 A | | 4/1986 | Pavelka | |
| 5,205,450 A | * | 4/1993 | Derosier | 224/161 |
| 5,497,922 A | * | 3/1996 | Tate | 224/160 |
| 5,666,432 A | | 9/1997 | Izumisawa | |
| 5,716,344 A | | 2/1998 | Kiel | |
| 5,728,070 A | | 3/1998 | Walker et al. | |
| 5,755,698 A | | 5/1998 | Kagan et al. | |
| 5,776,105 A | | 7/1998 | Corn | |
| 5,855,306 A | * | 1/1999 | Masak | 224/150 |
| 5,961,014 A | * | 10/1999 | Knerr | 224/153 |
| 5,988,315 A | * | 11/1999 | Crane | 182/3 |
| 6,164,505 A | * | 12/2000 | Holter et al. | 224/259 |
| 6,179,175 B1 | * | 1/2001 | Painter | 224/153 |
| 6,273,872 B1 | * | 8/2001 | Friedman | 604/174 |
| 6,524,288 B1 | * | 2/2003 | Hadley-Fruit | 604/322 |

* cited by examiner

*Primary Examiner*—Lee Young
*Assistant Examiner*—Maerena Brevard
(74) *Attorney, Agent, or Firm*—Patterson, Thuente, Skaar & Christensen, P.A.

(57) ABSTRACT

The present invention relates to strap assemblies. More specifically, the present invention relates to strap assemblies for supporting one or more devices mountable on an individual or patient, such as a drainage reservoir or other medical devices. Furthermore, the strap assemblies of the present invention are designed to alleviate some of the discomfort in wearing such an assembly. The strap assemblies of the present invention generally comprise a waist strap, a shoulder strap device and one or more front straps.

2 Claims, 6 Drawing Sheets

STRAP ASSEMBLIES AND METHODS OF USE THEREOF

CROSS-REFERENCE TO RELATED APPLICATION

This application is a completion application of U.S. Provisional Application Ser. No. 60/195,033, filed Apr. 6, 2000, and claims priority therefrom. U.S. Provisional Application Ser. No. 60/195,033 is also hereby incorporated by reference herein.

BACKGROUND OF THE INVENTION

The present invention relates to strap assembly. More specifically, the present invention relates to strap assembly for supporting one or more devices mountable on a patient, such as a drainage reservoir, electronic monitoring system, or other medical device. Furthermore the strap assembly of the present invention are designed to alleviate some of the discomfort in wearing such an assembly by utilizing a lightweight material that does not irritate the skin, but still possesses durable characteristics.

The prior art shows that a number of garments, harnesses and belts have been designed to support drainage reservoirs and similar type devices upon a patient's body. The utilization of support assemblies, such as garments, harnesses and belts, provide the patient with a means for positioning a device, such as drainage reservoir, lightweight tools or other similar devices, in an appropriate location and securing it there.

A supporting assembly for devices like a drainage reservoir is especially necessary in a post surgical period. For a period of time after a surgical procedure is performed on a patient, a drainage reservoir is required to be worn by a patient in order to drain away body fluids from the surgical site. In particular, one end of a drainage tube is positioned in the area of the surgical site while the other end is positioned in fluid communication with a drainage reservoir. Thus, excess fluids generated by the body at the surgical site as a result of the trauma of the surgical procedure is removed from the body.

As previously mentioned, various devices and methods have been used to support a drainage reservoir and are designed to be worn by a patient. For example, patients have used bulky garments or harnesses or single strap belts to support a drainage reservoir. Examples of garments or harnesses are disclosed in LaBove, U.S. Pat. No. 4,087,864, issued May, 9, 1978, Pavelka, U.S. Pat. No. 4,582,508, issued on Apr. 15, 1986, and Kagan et al., U.S. Pat. No. 5,755,698, issued on May 26, 1998. Each of these inventions provided support assemblies for drainage reservoirs, but were considerably bulky and restrictive to the wearer. Furthermore, the undesirability of these support assemblies becomes compounded when two or more drainage reservoirs are required to be worn by a patient.

An example of a belt support assembly is demonstrated in Kiel, U.S. Pat. No. 5,716,344, issued on Feb. 10, 1998. The belt disclosed in Kiel includes a single elastic strap that is secured around a patient's body. As the belt is secured to the patient's body it is threaded through a support loop attached to the drainage reservoir. While the support assembly disclosed by Kiel is lightweight and is not bulky it fails to sufficiently support the drainage reservoir. Slippage downward or around the body of the patient and away from the intended location is common with such belt support assemblies.

Furthermore, the use of belts as support assemblies, have been shown in the prior art to have additional disadvantages. One disadvantage is that most belts are not designed to allow the belt to be quickly and conveniently adjusted to the size of the patient. Moreover, some of these belts have been made of a material such as leather, which is inflexible, bulky, uncomfortable to a patient during use, and less able to withstand multiple washings in a washing machine.

Therefore, a need exists for an apparatus for supporting mountable devices, such as a drainage reservoir, which may be worn by the patient and is easy and convenient to use. What is further needed is an apparatus for supporting a mountable device, which is comfortable to wear. Additionally, what is needed is an apparatus for supporting a mountable device, such as a drainage reservoir, at a location adjacent to a patient's body, which eliminates the risk of injury and pain due to inadvertent movement of the apparatus that may dislodge the drainage reservoir and the drainage tubes adjoined to the drainage reservoir. Finally, a strap assembly is needed which can accommodate multiple mountable devices, such as drainage reservoirs, other medical devices, lightweight tools, sporting goods equipment, such as flies for fly fishing, etc.

SUMMARY OF THE INVENTION

A characteristic desired of a support assembly is that such an assembly may be configured to adequately secure a device mountable on a patient, such as a drainage reservoir, electronic monitoring device, lightweight tool or any other similar device, and in doing so also restricts movement of the device on a patient's body. A problem that exists with many secure support assemblies that possess these features is that they generally are bulky in appearance and lack comfort when worn by an individual. The strap assemblies of the present invention are intended to support one or more mountable devices, such as drainage reservoirs. Such mountable devices may be positioned and secured on the assembly to provide proper securement of the device, as well as, comfort for the wearer.

One embodiment of a strap assembly of the present invention comprises a waist strap, a shoulder strap device and one or more front straps. The waist strap is an elongated strip of fabric, which includes a first end and a second end. The waist strap extends around a patient's midsection and overlappingly secures to itself at the two ends. The waist strap ends normally include a loop material attached to the first end and a hook material attached to the second end.

Generally, the shoulder strap device includes, but is not limited to, a number of varying harnessing embodiments. A first embodiment is a halter configuration. The halter configuration is a single strap, which includes a loop and hook fastener or other attachment device, such as snaps, buttons, hook and pile devices or other similar fastening means, at each end.

In one embodiment of the present invention the halter strap end comprises a loop end. When the halter strap end includes a loop end, the waist strap is threaded through the two halter strap loop ends. A person wearing the support assembly would fasten the waist strap around the wearer's midsection and slip the attached halter strap over the head to a resting place upon the wearer's shoulders. It should be noted that the halter strap ends would normally be located on the front side of the wearer's midsection.

A second embodiment of the shoulder strap device is a suspender configuration. A general suspender configuration would generally include two straps, which have loops or attachment devices at each end. When loops are utilized as an attachment device, the waist strap may be threaded through the suspender strap loop ends. A person wearing the support assembly may fasten the waist strap around the wearer's midsection and pull the suspender straps over the shoulders so that each strap rests upon a different shoulder. The suspender straps may be crossed at the back of the wearer for additional support.

Finally, the segments of the halter strap or two suspender straps, which extend down the front of the wearer from the shoulders to the waist strap, are joined by one or more front straps. In one embodiment of the present invention, the front straps may comprise a strip of fabric with attachment devices on both ends for adjoining the front straps to the halter strap or suspender straps, or for releasable attachment to itself. Additionally, the front straps may be threaded through loops on the halter strap or suspender straps and secured to itself by loop material and hook material attached to opposite front strap ends.

The front straps are one of the structures generally utilized to secure the drainage reservoir or other mountable devices to the entire assembly and also further stabilizes the complete strap assembly system. By utilizing the front straps as a securing means for the mountable devices, such as drainage reservoirs, the mountable devices are better stabilized and can be located in more than one position on the front torso of the wearer. Furthermore, since the front straps give the complete assembly the ability to allow the mountable device, such as a drainage reservoir, to be located in more than one position, the strap assembly is also equipped for supporting multiple mountable devices.

Therefore, it is one object of the present invention to provide a new and useful assembly for supporting mountable devices, such as a drainage reservoir, which provides a more secure attachment to the wearer's body. The additional stability protects the wearer from injury or discomfort by further restricting the movement of the drainage reservoir.

It is another object of the present invention to provide an improved assembly for supporting mountable devices, such as a drainage reservoir, which is lightweight and not bulky.

Also, it is an object of the present invention to provide a strap assembly for supporting a mountable device, such as a drainage reservoir at a position adjacent to a patient's body, which may be more comfortable to a user.

It is a further object of the present invention to provide a new and useful strap assembly that can support multiple mountable devices, such as drainage reservoirs or support a mountable device in multiple positions on the front or back of the patient's or wearer's torso.

It is yet another object of the present invention to provide a strap assembly for supporting a mountable device, such as a drainage reservoir, which is easier to use.

It is moreover an object of the present invention to provide a strap assembly for supporting a mountable device, such as a drainage reservoir, which allows a patient to be more independent.

It is yet another object of the present invention to provide a strap assembly for supporting a mountable device, such as a drainage reservoir, which may be worn easily with a patient's clothing.

It is a further object of the present invention to provide a strap assembly for supporting a mountable device, such as a drainage reservoir, which can be quickly and conveniently secured to and released from a patient's body.

The above and other objects, features, and advantages of the present invention will become apparent from the following description and the attached drawings.

DETAILED DESCRIPTION OF THE INVENTION

While the invention is susceptible to various modifications and alternative forms, specific embodiments thereof have been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIGS. 1–8, there is depicted various embodiments of the strap assemblies 10 of the present invention. The assembly 10 includes a waist strap 11, a shoulder strap device 12 and one or more front straps 13. It should be noted that multiple front straps 12 may be utilized in the strap assembly 10. The assembly 10 is designed to support one or multiple mountable devices 15, such as drainage reservoirs, by attachment of the mountable devices 15 to either a front strap 13 or the waist strap 11.

Figure 2:
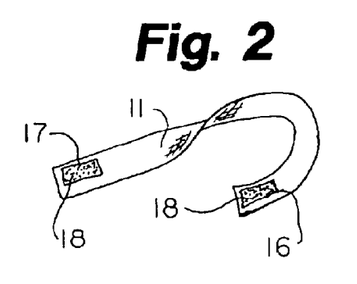
FIG. 2 is a perspective view of one embodiment of a waist strap or front strap.

FIG. 2 depicts one embodiment of the waist strap 11. The waist strap of the embodiment depicted in FIG. 2 may be an elongated strip of fabric, which includes a first end 16 and a second end 17. The waist strap 12 extends around a patient's midsection and overlappingly secures to itself at the two ends 16, 17. The waist strap ends include fasteners 18 attached to each end for releasably securing the two ends 16, 17 together. The fasteners for the assemblies of the present invention, preferably, comprise a loop material attached to the first end 16 and a hook material attached to the second end 17. A common loop and hook material used for such releasable attachment is Velcro®. Other suitable fasteners include hook and pile fasteners, snaps, buttons, strings and medical grade adhesives to just mention a few.

FIGS. 1, 3, 6 and 7 illustrates an embodiment of the strap assemblies 10, wherein the shoulder strap device 12 utilizes a halter design. The halter design comprises a single halter strap 19, which attaches to the waist strap 11 near the first waist strap end 16 and extends over and around the back of the neck and shoulders of the wearer to finally attach near the second waist strap end 17. Attachment devices 20 are utilized to adjoin the halter strap 19 to the waist strap 11. Examples of attachment devices 20 utilized in the present invention include, but are not limited to, hook and pile fasteners, snaps, buttons, strings, Velcro® and medical grade adhesives to just mention a few.

In a number of the embodiments of the present invention, the halter strap 19 is attached by a loop created when the halter strap is folded and overlapped upon itself until it may be attached at an attachment line 21 sufficient to provide a loop large enough to allow the waist strap 11 to be easily threaded through the loop. The overlapped portions of the halter strap 19 may be then connected, releasably or permanently, at one or multiple attachment lines 21 to create additional loops to accommodate front straps 13. The connection of the overlapping portions may be accomplished with an adhesive, snaps, stitching, buttons or any other suitable connecting means.

Figure 1:
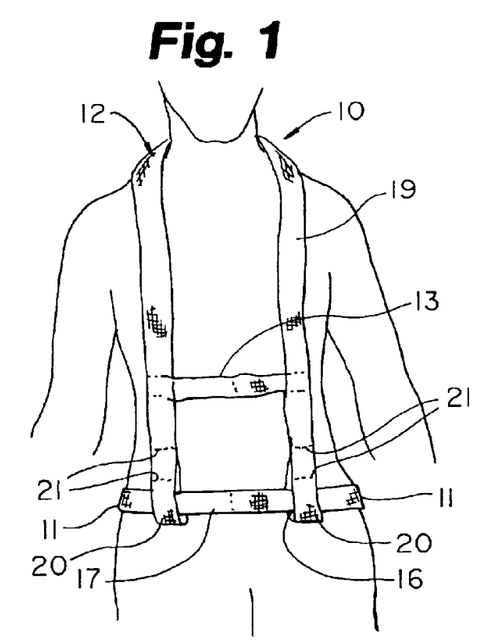
FIG. 1 is a perspective front view of one embodiment of a strap assembly of the present invention, which includes a halter design.

In one embodiment of the present invention, as depicted in FIG. 1, the overlapping portions extend for a longer distance on both ends 20 of the halter strap 18 so as to provide for multiple attachment lines 21 thereby creating multiple loops of approximately 1–2 inches in length. The multiple loops can be utilized for adjusting the size of the shoulder strap assembly and to accommodate one or more front straps. It is also noted that buckles (not shown) may be incorporated into the shoulder strap device for adjustment to various sized patients. Furthermore, Velcro® or other fastening materials may be attached to the inside of the loop and outside of the waist strap 11 or front straps 13 for additional securement of the waist strap 11 or front straps 13 to the strap assembly 10. FIGS. 1–8 illustrate that the waist strap 11 is threaded through the loops of the shoulder strap device 12.

Figure 3:
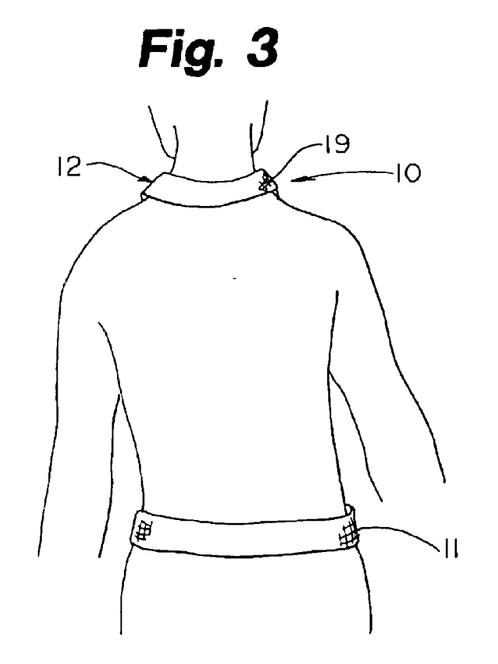
FIG. 3 is a perspective back view of one embodiment of a strap assembly of the present invention, which includes a halter design.
Figure 4:
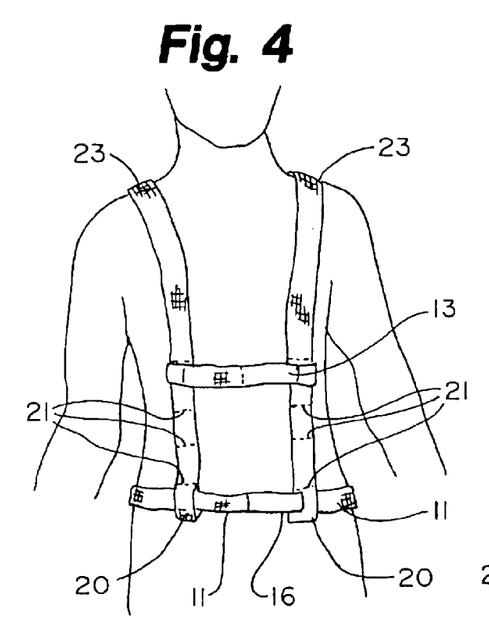
FIG. 4 is a perspective front view of one embodiment of a strap assembly of the present invention, which includes a suspender design.
Figure 7:
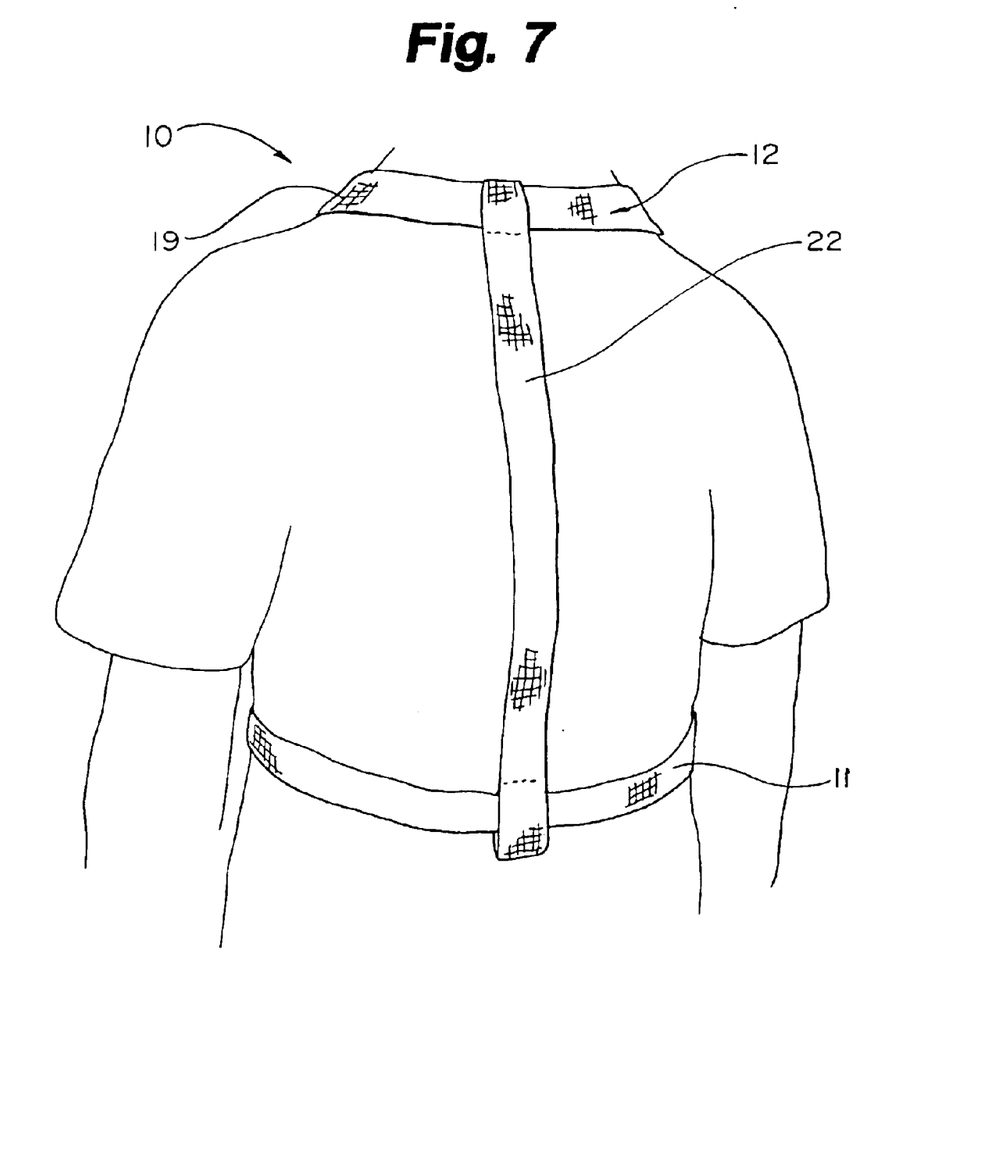
FIG. 7 is a perspective back view of one embodiment of a strap assembly of the present invention, which includes a halter design with a back strap.

FIGS. 3 and 7 depict the back of the strap assembly 10, which utilizes the halter design. FIG. 7 depicts an embodiment of the strap assembly 10 that includes an optional back strap 22 that may be attached to the middle of the halter strap 19 and extend down the wearer's back to an attachment at the middle of the waist strap 11. The back strap 22 may function to alleviate some of the pressure exerted upon the back of the neck and shoulders of the wearer.

The embodiments of the invention depicted in FIGS. 1–9, illustrate the straps used to create the waist strap 11, front straps 13 and shoulder strap device 12 as made of a material having a width of approximately one (1) inch and a light color such as white. However, any length and width that is suitable to fit the wearer of the assembly 10 is considered within the scope of the present invention. Furthermore, colors of the strap assemblies 10 may also vary.

Figure 5:
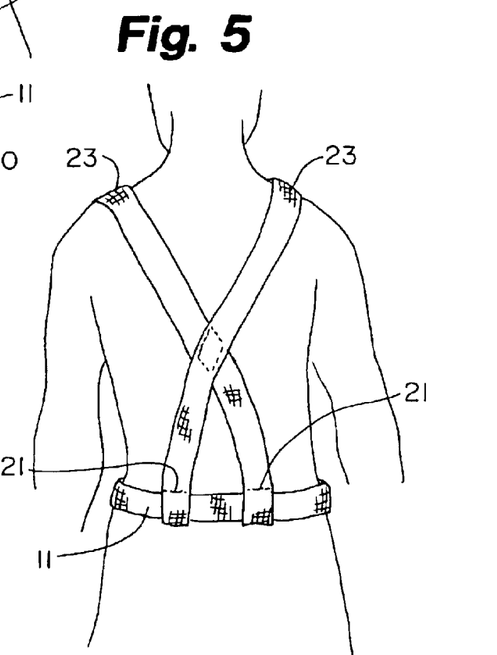
FIG. 5 is a perspective back view of one embodiment of a strap assembly of the present invention, which includes a suspender design.
Figure 5A:
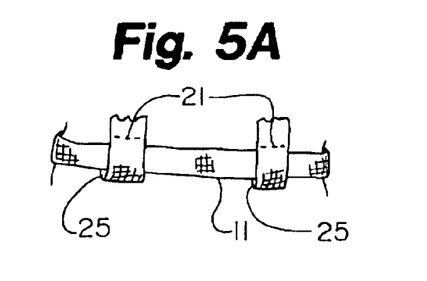
FIG. 5A is a perspective back view of one embodiment of a waist strap adjoined to a shoulder device that includes loops.
Figure 8:
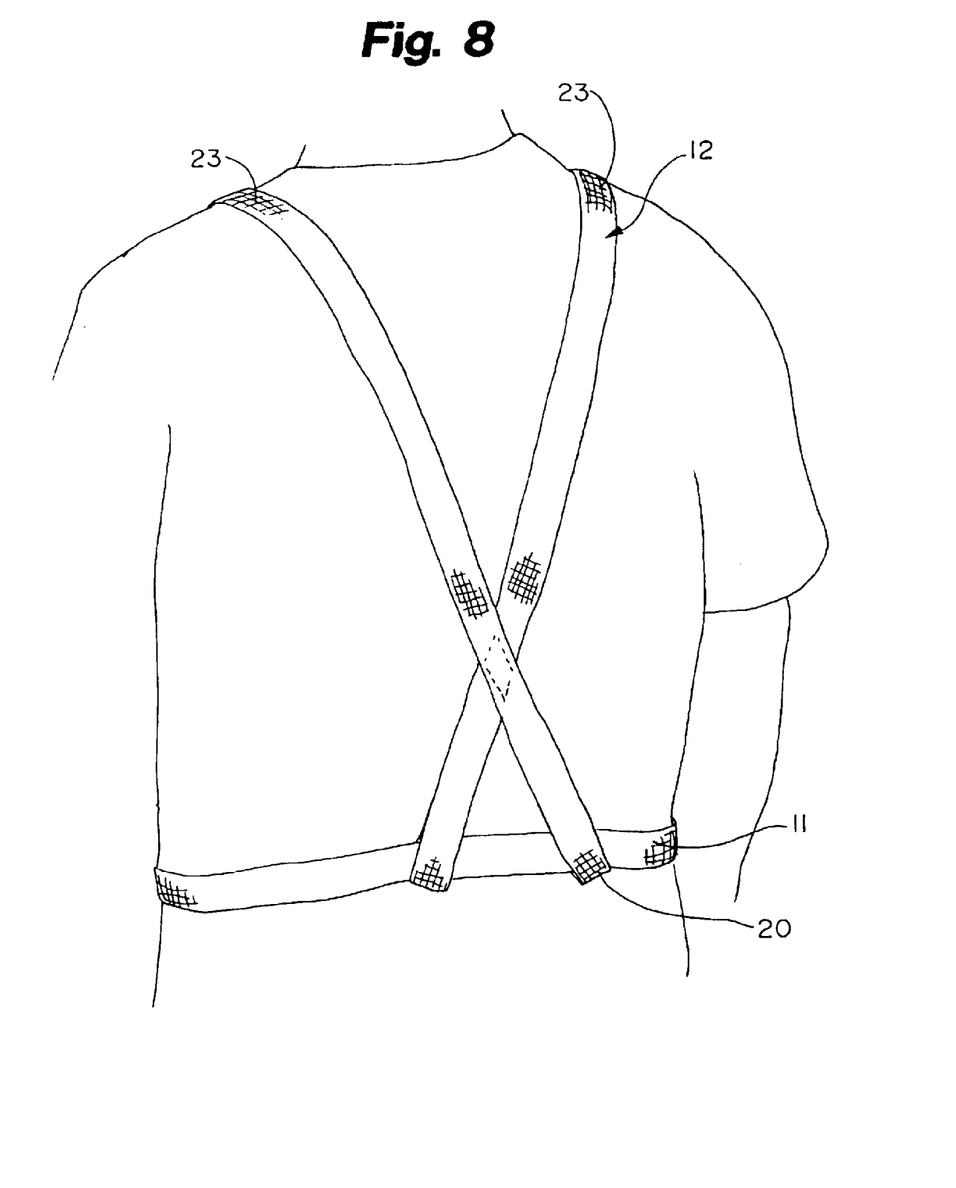
FIG. 8 is a perspective back view of one embodiment of a strap assembly of the present invention, which includes a suspender design that crosses the suspender straps.

FIGS. 4, 5, 8 and 9 illustrate another embodiment of the invention, which demonstrates the suspender configuration of the shoulder strap device 12. The suspender type of design generally includes two suspender straps 23. In the embodiment depicted in FIGS. 4 and 9 the suspender straps 23 attach to the waist strap 11 near the first waist strap end 16 and second waist strap end 17. The two suspender straps 23 are then extended over the shoulders of the wearer to finally attach to the waist strap 11 on the backside of the body of wearer as depicted in FIGS. 5 and 8. Attachment devices 20 operably adjoin the suspender straps 23 to the waist strap 11 and generally include, but are not limited to, hook and pile fasteners, snaps, buttons, strings, Velcro® and medical grade adhesives to just mention a few.

In the embodiments depicted in FIGS. 4, 5, 5A, 8 and 9, the suspender straps 23 are attached by one or more attachment devices 20 in the form of loops 25 created when the suspender straps are folded and overlapped upon themselves. The overlapped portions are then connected at one or more attachment lines 21 to create loops 25 at the suspender ends. The loops 25 function to attach the suspender straps 23 to the waist strap on the backside and the front side of the wearer's body in one or multiple locations. The connection of the overlapping portions at the attachment lines 21 may be accomplished with various connecting means including, but not limited to, adhesive, snaps, stitching, buttons or any other suitable connecting means.

The overlapping portions may extend for a distance on both ends of each suspender strap so as to create one or multiple loops of approximately 1–2 inches in length. However, other loop lengths may be utilized in the present invention to adequately accept varying waist strap and front strap widths. The multiple loops can be utilized for adjusting the size of the shoulder strap device 12 and to add one or more front straps 13 to the strap assembly 10. It is also noted that buckles (not shown) may be incorporated into the shoulder strap device for adjustment to various sized wearers or patients. Lastly, Velcro® or other fastening materials may be attached to the inside of the loops 25 for additional securement of the waist strap 11 or front strap 13. FIGS. 1–9 demonstrate that the waist strap 11 is threaded through the loops 25, thereby operably attaching the waist strap 11 to the shoulder strap device 12.

FIGS. 5 and 7 depict the back of the drainage reservoir strap assembly 10 which utilizes the suspender design. It should be noted that it is possible to cross the two straps on the back of the wearer before attachment to the waist strap on the back of the wearer. Such a cross section may optionally be secured by stitching or any other means of connection including Velcro® or an adhesive.

As shown in FIGS. 1, 3, 5 and 8, the shoulder strap device 12 is joined on the front of a person's body by one or more front straps 13. The front straps 13 may comprise of the same material as used to make the waist strap 11 and shoulder strap devices 12, but may also be produced using an alternated material which may further stabilize the drainage reservoir, such as a more rigid rubber, vinyl or plastic material. In one embodiment the front strap 13 includes fasteners 18 similar to the fasteners utilized to releasably secure the waist strap 11 around the midsection of the wearer. In one embodiment of the present invention, the front strap 13 may resemble the waist strap 11 depicted in FIG. 2 with the exception being the difference in length (The front strap 13 is generally shorter than the waist strap). In one embodiment, a fastener 18 that may be utilized with the front straps comprises a loop material attached to one end of the front strap 13 and a hook material on the other end of the front strap 13. It is noted that the fasteners 18 can be any type of releasable connection means including the fasteners previously described in connection with the waist strap.

Figure 6:
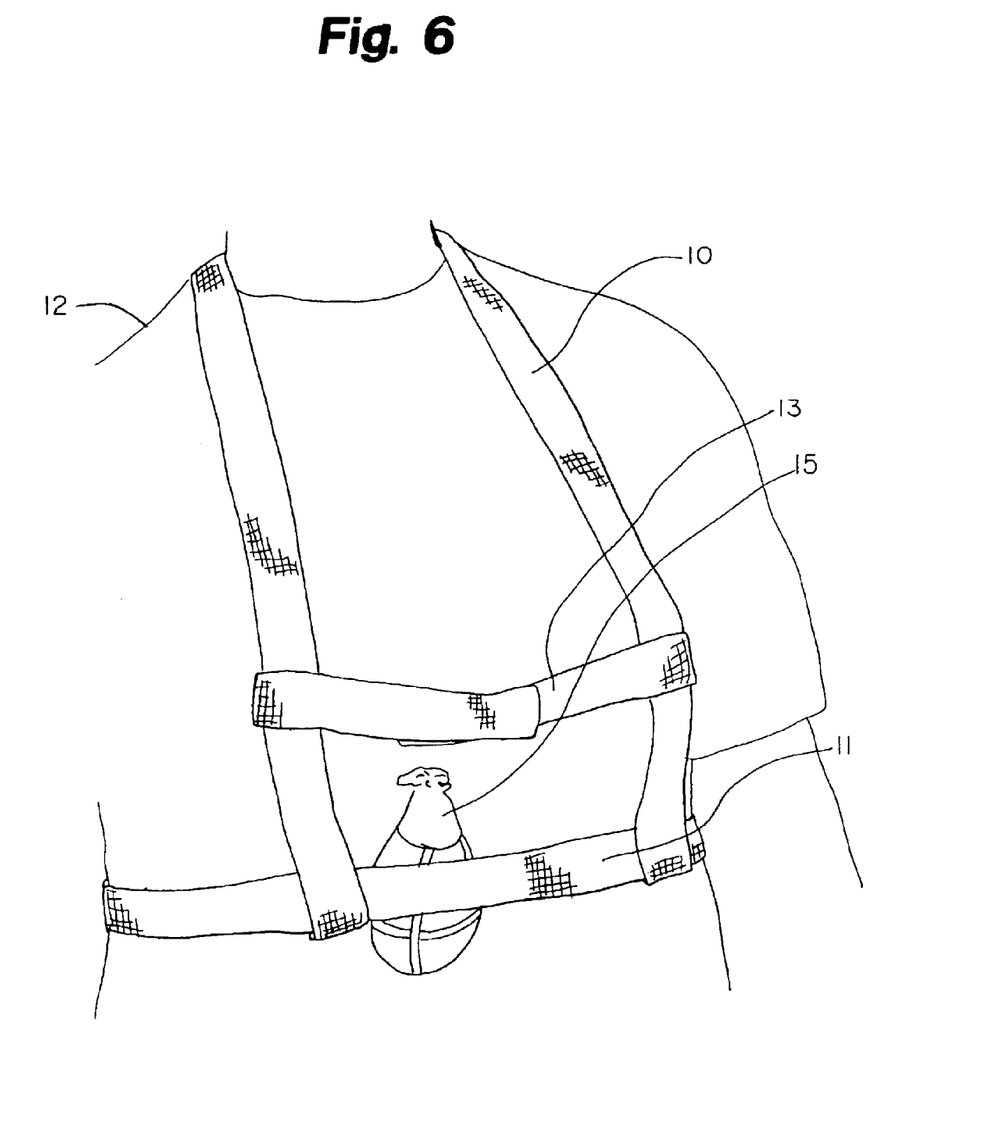
FIG. 6 is a perspective front view of one embodiment of a strap assembly, which includes a halter design and is supporting a mountable device.
Figure 9:
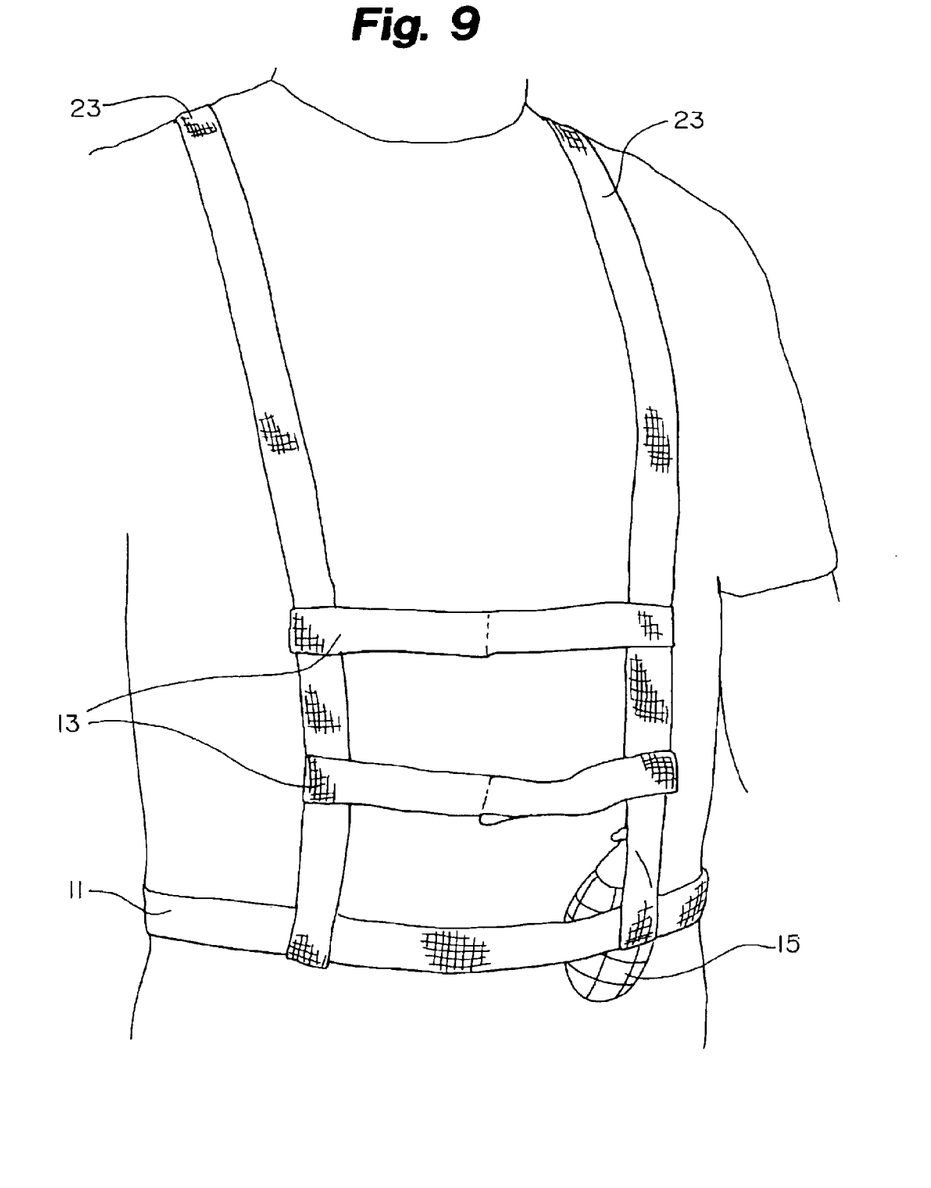
FIG. 9 is a perspective front view of one embodiment of a strap assembly, which includes a suspender design and is supporting a mountable device.

Referring to the embodiments depicted in FIGS. 6 and 9, when incorporating the front straps 13 into the strap assembly 10, the front straps 13 are threaded through the loops present on the shoulder device 12 and located on the front of the wearer's body. It is noted that loops may also be placed on the portions of the halter strap 19 and shoulder straps 23 proximate to the back of the wearer, thereby accommodating front straps 13 positioned on the back of the wearer. Once threaded through the loops, the front straps 13 are folded and releasably secured upon itself using the fasteners 18 present at opposite ends of the front strap 13. It is also recognized that the front strap 13 may be attached directly to the halter or shoulder straps using any type of connection means or fasteners previously described or used for similar devices.

When it is desired to locate a mountable device 15, such as a drainage reservoir, at a location adjacent to a patient's body as shown in FIGS. 5–8, the strap assembly 10 is first positioned on the wearer or patient. Next, a front strap 13 or the waist strap 11 is advanced through a support loop attached to the mountable device 15. Other means of attaching the mountable device 15 could be exercised, but the previously described means corresponds to the drainage reservoir devices produced presently. Therefore, adjustment could be made for other mounting fasteners present on any manufactured mountable device 15, such as a drainage reservoir. Thereafter, the front strap 13 or waist strap 11 is then stretched so that the fasteners 18 may be adjoined. For example, the loop fastener on the waist strap 11 or front strap 13 may be brought into contact with the corresponding hook fastener on the waist strap 11 or front strap 13 so as to form an engagement therebetween. As a result of the above activity, a portion of the support loop of the mountable device 15, such as a drainage reservoir, is tightly interposed between the body and either the front strap 13 or waist strap 11. Finally, as previously mentioned, the flexibility of locating multiple front straps 13 on the drainage reservoir strap assembly 10 provides additional attachment positions for multiple mountable devices, such as drainage reservoirs or the positioning of a single mountable device in a multitude of potential locations.

The strap assembly 10 of the present invention can be easily and economically manufactured of various materials so as to provide a safe and convenient method of storing and receiving mountable devices 15, such as drainage reservoirs. Furthermore, the strap assemblies 10 described above can be mass produced or custom manufactured without difficulty from a variety of readily available and inexpensive materials, including, but not limited to, cloth, plastics of various types, leather, rubber or the like, vinyls, and/or paper-type products, including paper products which would be more or less disposable in nature. Typically, a woven fabric may be used which is adapted for repeated washing and drying in household appliances making for effortless clean-up. A reasonably comfortable, elastic or elasticized primarily cotton material, or equally desirable alternative, of the desired solid color or with a desired pattern of color(s) and or design(s) is preferred. The material is generally naturally non-irritating to the skin of most adults, children and infants.

In one embodiment of the invention, an elastic or elasticized, primarily cotton material is employed to ensure a snug fit; although such is not required in light of the many inexpensive and desirable alternatives. The loop and hook fastening means employed for front straps 13 and waist straps 11 allow for an adjustable configuration, which would permit a comfortable snug fit without the use of an elastic material. The primarily cotton or other equally desirable alternative material may be pre-treated with suitable chemicals and or treatments which are known to prevent or resist staining, absorption or degradation upon exposure to blood, medical or other bodily fluids and substances. Other reusable and disposable materials are readily available (e.g. those presently used for hospital gowns, surgical smocks and masks), which are well suited for construction of this invention. In fact, health care facilities concerned with infection control and minimization of waste materials may in some short-term care or high-infection-risk situations prefer more inexpensive, disposable materials which are easily disinfected, incinerated or otherwise disposed of within the capabilities of existing nosocomial systems.

While an elastic or elasticized, absorbent, soft and breathable primarily cotton material is often preferred for those portions of the strap assembly 10 in contact with the patient's skin, the front straps 13, may be constructed entirely or in combination with a plastic, plasticized or other material treated by methods known to the art. Such front straps 13 result in the front straps 13 being incapable of or resistant to staining, absorption, or deterioration caused by exposure to blood, medical or other bodily substances. Furthermore, this type of front strap 13 may be designed for quick and easy cleaning such that the entire strap assembly 10 need not be cleaned every time medical fluids or blood contact the front strap material.

While the invention has been illustrated and described in detail in the drawings and foregoing description, such an illustration and description is to be considered as exemplary and not restrictive in character, it being understood that only the preferred embodiments have been shown and described and that all changes and modifications that come within the spirit of the invention are desired to be protected.

What is claimed is:

1. A method of supporting one or more mountable post-surgical drainage reservoirs with drainage tubes on an individual comprising:

positioning on the upper torso of an individual a strap assembly comprising a waist strap including first and second ends, fasteners attached to the first and second ends for releasably connecting said first end to said second end, a shoulder strap device including one or more straps adjoined to said waist strap in at least two positions, wherein the shoulder strap device includes loop ends for threaded attachment with the waist strap and substantially vertical frontal portions, and wherein said substantially vertical frontal portions include one or more attachment points formed by loops for attachment of one or more front straps, and one or more front straps releasably adjoined to the shoulder strap device at said loops;

mounting the one or more mountable post-surgical drainage reservoirs with drainage tubes to said one or more front straps, waist strap or both; and securing the waist strap and front straps.

2. A method of supporting one or more mountable post-surgical drainage reservoirs with drainage tubes on an individual comprising:

positioning on the upper torso of an individual a strap assembly comprising a waist strap including first and second ends, fasteners attached to the first and second ends for releasably connecting said first end to said second end, a shoulder strap device including one or more straps adjoined to said waist strap in at least two positions, wherein the shoulder strap device includes substantially vertical frontal portions, and wherein said substantially vertical frontal portions include a plurality of loops formed by overlapping of the frontal portions on themselves for attachment of the waist strap and one or more front straps, and one or more front straps releasably adjoined to the shoulder strap device, wherein the one or more front straps include a loop material and hook material for releasably securing the front strap to the shoulder strap device;

mounting the one or more mountable post-surgical drainage reservoir with drainage tubes to said one or more front straps, waist strap or both; and securing the waist strap and front straps.

* * * * *